United States Patent
Binder et al.

(10) Patent No.: US 7,101,349 B2
(45) Date of Patent: *Sep. 5, 2006

(54) FLEXIBLE SUPPORT FOR GEL WRAPS

(75) Inventors: David M. Binder, Richmond, VA (US); Edward C. Leicht, Goleta, CA (US); William J. Binder, Beverly Hills, CA (US)

(73) Assignee: GelZone, Inc., Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/825,766

(22) Filed: Apr. 16, 2004

(65) Prior Publication Data

US 2005/0027228 A1    Feb. 3, 2005

Related U.S. Application Data

(62) Division of application No. 09/931,974, filed on Aug. 17, 2001.

(60) Provisional application No. 60/226,602, filed on Aug. 21, 2000.

(51) Int. Cl.
*A61F 13/00* (2006.01)
(52) U.S. Cl. .............. 602/75; 602/77; 602/48; 602/42; 602/58
(58) Field of Classification Search ............. 602/41–77
See application file for complete search history.

(56) References Cited

U.S. PATENT DOCUMENTS

| | | | | |
|---|---|---|---|---|
| 4,024,312 A | 5/1977 | Korpman | | 428/343 |
| 4,377,160 A | 3/1983 | Romaine | | 128/156 |
| 4,671,267 A | 6/1987 | Stout | | 128/156 |
| 4,675,009 A | 6/1987 | Hymes et al. | | 604/304 |
| RE32,991 E | 7/1989 | Szycher et al. | | 528/75 |
| 4,941,464 A | 7/1990 | Scott | | 128/84 R |
| 4,991,574 A | 2/1991 | Pocknell | | 128/156 |
| 5,156,601 A | 10/1992 | Lorenz et al. | | 604/307 |
| 5,340,363 A * | 8/1994 | Fabo | | 604/304 |
| 5,419,913 A | 5/1995 | Podell et al. | | |
| 5,501,661 A | 3/1996 | Cartmell et al. | | 602/58 |
| 5,540,922 A | 7/1996 | Fabo | | 424/402 |
| 5,603,145 A | 2/1997 | Arakawa et al. | | 24/442 |
| 5,635,201 A | 6/1997 | Fabo | | |
| 5,656,279 A | 8/1997 | Dillon | | 424/402 |
| 5,674,523 A | 10/1997 | Cartmell et al. | | 424/445 |
| 5,759,560 A | 6/1998 | Dillon | | 424/402 |
| 5,843,018 A | 12/1998 | Shesol et al. | | 602/79 |
| 5,891,076 A | 4/1999 | Fabo | | 602/52 |
| 5,895,656 A | 4/1999 | Hirshowitz et al. | | 424/402 |

(Continued)

FOREIGN PATENT DOCUMENTS

EP    0 528 091    2/1993

OTHER PUBLICATIONS

Int'l Search Report dated Oct. 29, 2003 for PCT/US03/01287.

(Continued)

*Primary Examiner*—Tatyana Zalukaeva
*Assistant Examiner*—Keshia Gibson
(74) *Attorney, Agent, or Firm*—Drew Wintringham; Clifford Chance US LLP

(57) ABSTRACT

A two-ply bandage for treatment of skin while providing orthopedic support having a first layer of gel for contacting the skin and a second layer of an elastic and supportive loop portion of a hook and loop fastener. The product is economically manufactured in the form of long rolls or as a sheet and is easily cut to any desired shape.

23 Claims, 4 Drawing Sheets

U.S. PATENT DOCUMENTS

| | | | |
|---|---|---|---|
| 5,919,476 A | 7/1999 | Fischer et al. | 424/443 |
| 5,980,923 A | 11/1999 | Dillon | 424/402 |
| 6,143,946 A | 11/2000 | Docter | 602/41 |
| 6,506,175 B1 * | 1/2003 | Goldstein | 602/60 |

OTHER PUBLICATIONS

Upper Extremities, Silipos, vol. III, 1998 pp. 1-7.

Epi-Derm Silicone Gel Sheeting, State of the Art Treatment for Keloids and Hypertrophic Scars.

International Search Report dated Jun. 12, 2002 for PCT/US01/25715.

Partial EP Search Report for Corresponding EP. App. No. 01965969.7 dated Mar. 15, 2006.

* cited by examiner

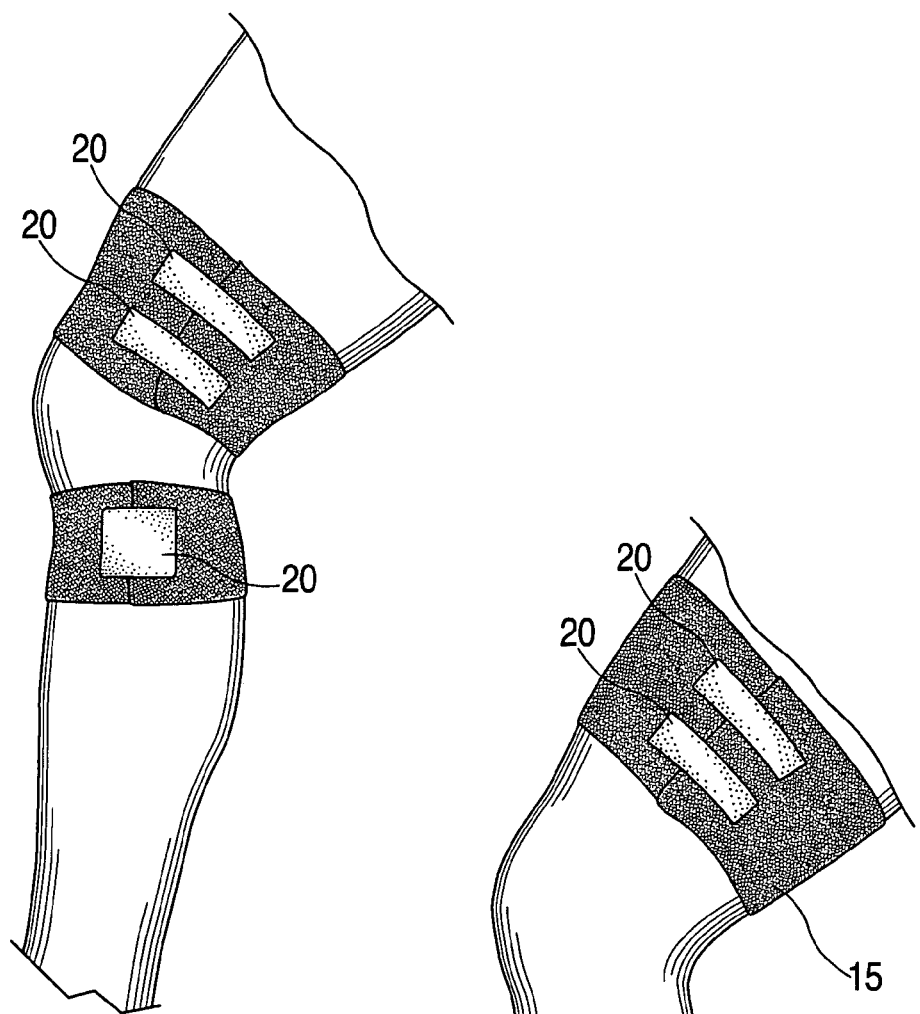

FLEXIBLE SUPPORT FOR GEL WRAPS

This application is a continuation of Ser. No. 09/931,974 filed Aug. 17, 2001, now allowed, which is a non-provisional application which claims the benefit of U.S. Provisional Application No. 60/226,602 filed Aug. 18, 2000.

BACKGROUND OF THE INVENTION

The present invention relates to a medical or surgical bandage suitable for use in providing musculo-skeletal support and treatment of skin conditions.

SUMMARY OF THE INVENTION

The invention relates to positioning a gel against the skin utilizing a stretchable bandage that also provides the added benefit of orthopedic, or musculo-skeletal, support for the joint or portion of the body on which the bandage is wrapped.

More specifically, this invention relates to a composite material consisting of two layers; a layer of gel bonded to a stretchable carrier layer of a rigid and elastic loop portion of a hook and loop fastener. The stretch carrier layer is useful for positioning the gel layer in place on the body while at the same time providing substantial musculo-skeletal support to the portion of the body around which the bandage is wrapped.

This invention relates to a composite structure which incorporates the pressure therapy features of a rigid yet stretchable carrier material with a silicone gel for treatment of skin conditions. Silicone gel materials are used in the medical field for the management of such conditions, for example, as dermal scarring, varicose veins and stasis ulcers. These silicone materials soften scar tissue and improve the cosmetic as well as functional aspects of scars for instance.

There is a need in the medical and veterinary fields to combine supportive (pressure) therapy with a gel treatment, particularly on the extremities of the body. In the case of veterinary applications, fur is used herein interchangeably with skin. Supportive pressure therapy is useful, for example, to provide musculo-skeletal support for joints and muscles, and in the treatment of carpal tunnel syndrome, arthritis and tennis elbow. This is not easy or convenient under present methods. Typically in the medical and veterinary fields supportive pressure therapy is provided using compression garments or wraps. When used with a gel, a person must typically apply a layer of gel to the area of the body to be treated followed by wrapping another material such as a compression garment or wrap to keep the gel in position. The materials typically used don't provide the elastic support usually desired and therefore require many wraps of the material. Furthermore, typical materials lose much of their elasticity after only a couple of uses.

Hook and loop fasteners are now available with rigid yet stretchable loop portions that have a modulus of elasticity of about 50%, with no stretch memory. The strong elastic property provided by the stretchable loop portion makes it possible for a bandage using this material to be wrapped only once around a part of the body while maintaining contact with the skin to be treated. By applying a surface layer of silicone gel to the flat side (non-loop surface) of a stretchable loop portion of a hook and loop fastener, it was discovered that bandages can be produced which provide a surface layer of silicone for uniform skin contact with the added benefit of musculo-skeletal support. The bandage of this invention having a stretchable loop portion as the carrier layer for the gel can therefore follow the many shapes and anatomical contours of the body while at the same time providing secure positioning of the gel on the skin of the user. The combination of stretch carrier and gel layer provides greater comfort to the user because the bandage allows for movement and flexing of the body without reduction in the bandages effectiveness, i.e. support and resistance to slipping. Thus, the support provided by this invention offers the wearer of the bandage greater comfort and durability and makes for the ideal bandage for repeated usage and/or usage over long periods of time.

This invention is an improvement over the prior art in that (a) the carrier material is rigid and elastic so that substantial orthopedic support (i.e., musculo-skeletal support) is provided by just a one layer wrapping, (b) the product is far more durable than Lycra® (synthetic fibers and filaments for generalized use in the industrial arts) and other known, thin elastic based products commonly available, (c) both pressure and silicone therapies may be applied concomitantly by this invention and therefore eliminating a separate and/or repeated process of fitting more than one material individually, and (d) patient compliance may be improved because continued, even long term, comfortable use of the product is possible without loss of support from the carrier material. Furthermore, the carrier of the present invention provides the added benefit of a bandage that supplies even pressure to the body across the area of the bandage being treated.

The manufacturing process of this invention lends itself to large-scale production in either flat sheets or long rolls. Final shapes of limitless configurations can then easily be cut from the sheets or rolls. This provides for rapid and cost effective production of custom-made shapes for any given application or patient.

BRIEF DESCRIPTION OF THE DRAWINGS

FIG. 7 is a perspective view illustrating the use of particular embodiments of this invention adjacent to the knee joint of a user.

FIG. 8 is a perspective view illustrating the use of an embodiment of the, present invention about the thigh of a user, and showing loop surface 15 of the bandage and closure strips 20.

DETAILED DESCRIPTION OF THE INVENTION

Figure 1:
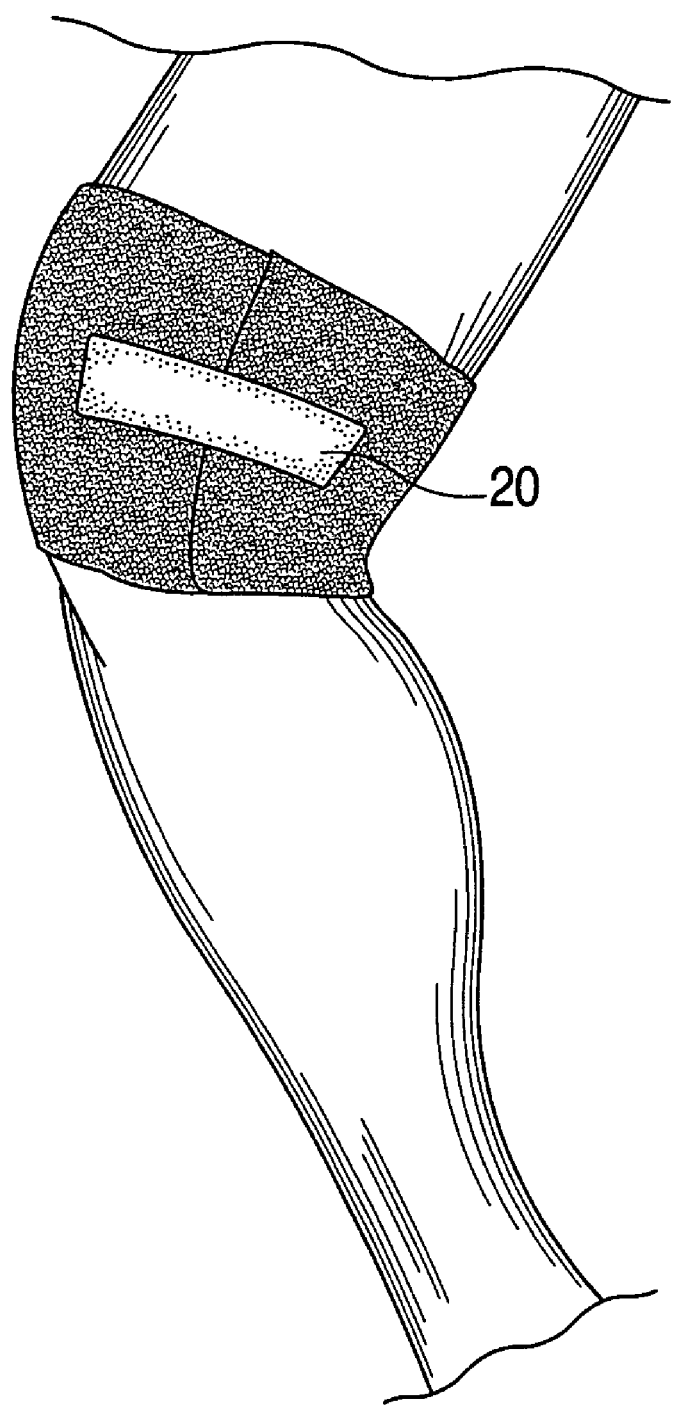
FIG. 1 is a perspective view illustrating the use of one embodiment of this invention on the knee of a user.
Figure 2:
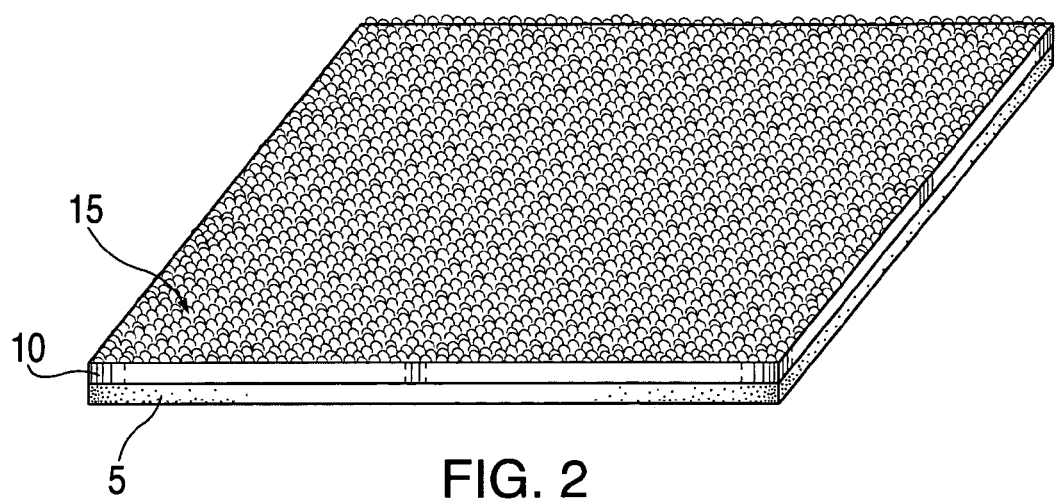
FIG. 2 is an embodiment illustrating gel layer 5 bonded to carrier 10, having a loop surface 15, bonded to gel layer 5.
Figure 3:
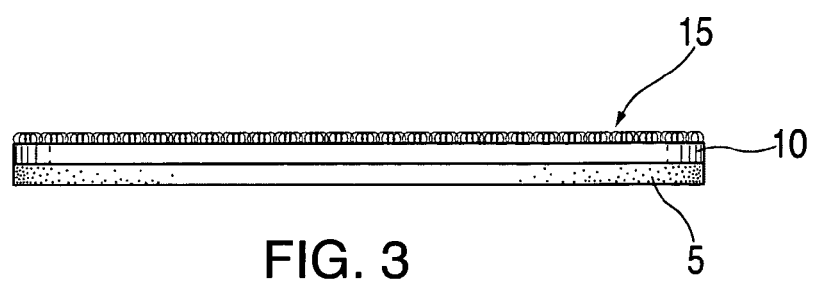
FIG. 3 illustrates carrier 10, having loop surface 15, bonded to gel layer 5.
Figure 4:
FIG. 4 illustrates closure strip 20

The description provided below references FIGS. 1 through 8 as part of the disclosure and the associated reference numerals.

The device of the present invention, shown in FIGS. 1 through 3, 7 and 8, is generally described as a rigid yet stretchable bandage with a silicone gel coating 5 on one side. The carrier 10 is a thick, stretchable loop portion of a hook-and-loop fastener such as Velcro®. In a particular embodiment, carrier 10 is about ⅛ inch thick. The silicone gel used in gel 5 is commercially available as either a 1:1, 3:1, or 10:1 mixture of a polydiorganosiloxane resin and a catalyst. Generally speaking, the silicone gel is an addition cured polydimethyl-siloxane gel. This type of gel is well described in the literature, including some of the existing patent literature (e.g. U.S. Pat. No. 4,991,574 ("Pocknell") which is incorporated herein by reference). There is no particular reason to limit our device to silicone gel, if there are other gels that provide clinical benefit. Further, additives may be introduced into the gel, including, for example, oils, BEN GAY® (medicinal preparations to be applied externally for use in the treatment of rheumatism, muscular aches and pains, neuralgia, minor bronchial irritations, coughs and throat irritations due to colds) and other topical medications and emollients that seep into the skin area on which the gel is applied. Although other gels may be used, silicone gel has the special benefit of reducing the appearance of hypertrophic and keloid scarring. The advantages of silicone gel are widely known and are also well described in the existing patent literature (e.g. U.S. Pat. No. 5,759,560 ("Dilon"), U.S. Pat. No. 5,656,279 ("Dillon"), and U.S. Pat. No. 5,895,656 ("Hirschowitz et al.") all the contents of which are herein incorporated by reference. Silicone gel is also known to be hydrophobic, so it won't break down or change characteristics in the presence of water or sweat. Cured silicone gel is cohesive (retains its shape) but is not very strong. It can be easily torn, and to be handled by the average person, it must be reinforced with some alternate carrier material.

In the present invention, carrier 10 is preferably a commercially available loop portion of a stretchable hook-and-loop fastener such as, for example Velstretch®. This "stretch" carrier is essentially the traditional loop portion of a hook-and-loop fastener woven with an elastic material. Depending on the degree of "stretch" needed, different elastic interweaves may be used, and from which a stretch of approximately 50% in one direction may be obtained. This carrier, or substrate, provides the backbone, or compressive force, necessary to apply the silicone gel to any contour on the body, especially joints, both large and small, while also providing the benefit of support to the underlying tissue. The thickness of the carrier also provides support to the joint, so that the pain and discomfort of joint inflammation due to a variety of medical conditions is minimized. An added benefit of the carrier is to provide protection, for example, from abrasion, to the surface of the skin upon which the invention is applied. The support and protective aspects of the present invention, as described above, easily lend themselves to uses on animals as well.

In a particularly preferred embodiment, the opposed surface of the "fuzzy" side or "loop" side 15 of the carrier 10 is used as the carrier for the gel.

The bandage may be secured about the afflicted joint or area of the body with a complimentary strip of the hook portion 20 (FIG. 4) of a hook and loop fastener material which may be used to keep the bandage closed around the joint or area of the body. Multiple strips or one large strip of width equal to approximately the width of the bandage may also be used to provide proper securing of the bandage as shown in FIG. 7.

In one particularly preferred embodiment, the combined product of this invention has the "loop" side, or loop portion 15 (the soft side), of the stretch carrier 10 on one side and a layer of silicone gel on the other. The gel goes against the skin, and the product is fixed in place by wrapping the body portion with the bandage and applying a complimentary "hook" or closure strip 20 of fastener material at any point along the bandage seam.

An embodiment of this invention could be provided in a roll form, about 3" wide by about 1 foot long for applications such as those currently employing use of an Ace® type bandage. In this configuration, the present invention can replace the application of Ace-type bandages for musculoskeletal support and other orthopedic bandages which are specially configured to fit knees, ankles, wrists, elbows, and other problematic joints. Other dimensions applicable to specific applications are also contemplated, such as for use around a thigh or forearm.

It is an embodiment of the present invention for the stretchable carrier 10 to provide a platform for the gel to be continuously applied against any existing scar, which will in turn provide the widely understood benefit of reduced scar appearance. Because the gel is deposited on the carrier 10 while the carrier 10 is in the un-stretched position, it should be understood that, as the carrier 10 is expanded, the gel also expands in the same direction. This will allow air to circulate into the treated area, reducing discomfort due to sweating, yet still provide the benefit of the gel applied against the scar. Further, as the carrier 10 is expanded and then closed using the hook section, the carrier 10 provides compression and support to the affected area.

The silicone gel provides an additional comfort factor of "coolness" against the skin, which is not diminished to any large degree by keeping the present invention in place for the required period. Because the present invention is comfortable, supportive, adaptable, stretchable, trimmable, usable on any joint or area of the body around which it can be wrapped, it is expected to result in higher patient compliance with the treatment.

Figure 5:
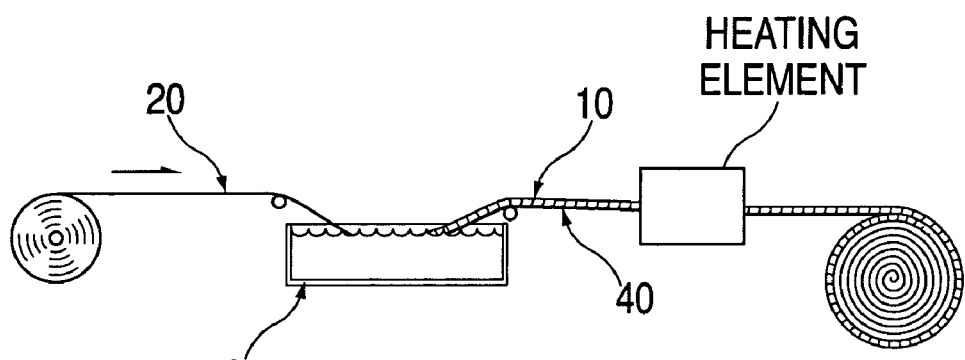
FIG. 5 illustrates a method of manufacture using gel bath 30, carrier 10, and heating element 50.

A method of manufacturing the present invention is shown in FIG. 5, and described as follows.

The desired gel is mixed as designated by the material manufacturer, i.e. 1:1, 3:1, or 10:1 parts resin and catalyst, although the mixture can be varied to obtain different degrees of tack from the final cured gel. The mixture is poured onto a flat surface, such as large sheet of polycarbonate, and allowed to settle until it is a consistent thickness. The gel, after having been allowed to settle, has a consistent thickness and is surrounded by an appropriate sized wall to contain the gel on the polycarbonate surface. In one embodiment, the gel thickness is approximately 2 mm, although the thickness may vary from as little as 0.5 mm up to 4 mm. Meanwhile, the carrier 10 may be washed in a mild soapy solution such as Ivory® soap to remove the oils and agents used in processing the fabric, and allowed to air dry. After the gel is settled to a consistent thickness (about 20–60 minutes) the dry carrier 10 is placed on top with the loop surface of the carrier 10 away from the gel. The assembled materials are then allowed to cure. In a preferred embodiment, the combined gel and carrier 10 are placed in an oven 50 for 1–3 hours and at a temperature of about 100 to 180 degrees centigrade until the gel is cured. The cured, assembled materials are then removed from the oven 50 and can then be cut into any shape desired.

The present invention also lends itself well to mass production by coextrusion as shown in FIG. 5. In this embodiment, stretchable carrier 10 is continuously unrolled from a large roll of material onto a bath 30 of gel. As the carrier 10 is removed from the bath 30 a layer of gel 40 adheres to the carrier 10 and settles to a uniform thickness. The stream of combined carrier/gel is then passed through a heating oven 50 and cured. At the other end of the oven 50 are take-up rolls and/or cutting fixtures to facilitate rolling or cutting the cured product into any desired configuration.

Figure 6:
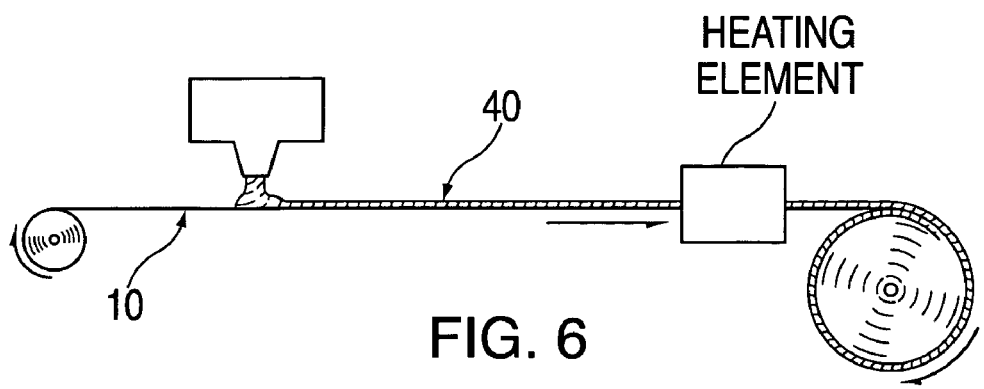
FIG. 6 illustrates a river of carrier 10, uncured gel compound 40, and heating element 50.

In another embodiment shown in Fig 6, an amount of gel 40 is deposited onto a river of carrier 10 as the carrier 10 passes beneath the gel. A layer of gel is formed on the side of the carrier 10 opposite the loops and the gel is allowed to settle to a uniform thickness. The river of combined carrier/gel material is then passed through a heating oven 50 and cured. At the other end of the oven 50 are take-up rolls and/or cutting fixtures to facilitate rolling or cutting the cured product into any desired configuration.

Using either of the previous embodiments, there are specific production techniques which will result in a consistent layer of gel being applied to the flat side of the stretch carrier 10, opposite the loop side.

What is claimed is:

1. A method for providing musculo-skeletal support, which comprises the steps of:
   (a) wrapping a stretchable, supportive laminate wrap around a portion of a body in need of musculo-skeletal support, wherein the laminate wrap comprises a silicone gel having a skin contacting surface, said silicone gel being laminated to an elastic carrier wherein said carrier is the loop portion of a hook and loop fastener, said laminate wrap forming an integrated structure configured to have elasticity sufficient to provide compression against a body surface without substantial fragmentation of said silicone gel;
   (b) stretching the laminate wrap around the portion to be supported; and
   (c) securing the laminate wrap in a closed position with one or more closure strips.

2. The method of claim 1, wherein the elastic carrier has a modulus of elasticity of about 50%.

3. The method of claim 1, wherein the laminate wrap is a bandage for a joint or a muscle.

4. The method of claim 3, wherein the joint is a knee, an ankle, a wrist, or an elbow.

5. The method of claim 4, for use in the treatment of carpal tunnel syndrome.

6. The method of claim 4, for use in the treatment of arthritis.

7. The method of claim 4, for use in the treatment of tennis elbow.

8. The method of claim 3, for use in a veterinary application.

9. The method of claim 3, wherein the closure strip is approximately the width of the bandage.

10. The method of claim 1, wherein the silicone gel is a cured polydiorganosiloxane resin.

11. The method of claim 10, wherein the gel contains an additive.

12. The method of claim 11, wherein the additive is a topical medication or an emollient.

13. A method for providing musculo-skeletal support, which comprises the steps of:
   (a) wrapping a stretchable, supportive laminate wrap around a portion of a body in need of musculo-skeletal support, wherein the laminate wrap comprises a gel having a skin contacting surface, said silicone gel being laminated to an elastic carrier wherein said carrier is the loop portion of a hook and loop fastener, said laminate wrap forming an integrated structure configured to have elasticity sufficient to provide compression against a body surface without substantial fragmentation of said gel;
   (b) stretching the laminate wrap around the portion to be supported; and
   (c) securing the laminate wrap in a closed position with one or more closure strips;
   wherein the closure strip is the hook portion of a hook and loop fastener.

14. The method of claim 13, wherein the gel is a silicone gel.

15. A method for providing a skin treatment, which comprises the steps of:
   (a) wrapping a stretchable, supportive laminate wrap around a portion of a body having skin in need of treatment, wherein the laminate wrap comprises a gel having a skin contacting surface, said silicone gel being laminated to an elastic carrier wherein said carrier is the loop portion of a hook and loon fastener, said laminate wrap forming an integrated structure configured to have elasticity sufficient to provide compression against a body surface without substantial fragmentation of said gel;
   (b) stretching the laminate wrap around the portion of the body to be treated; and
   (c) securing the laminate wrap in a closed position with one or more closure strips.

16. The method of claim 15, wherein the gel is a silicone gel.

17. The method of claim 15, wherein the carrier has a modulus of elasticity of about 50%.

18. The method of claim 15, wherein the closure strip is the hook portion of a hook and loop fastener.

19. The method of claim 15, wherein the laminate wrap is a bandage and wherein the skin treatment reduces the appearance of scarring.

20. The method of claim 15, wherein the silicone gel is a cured polydiorganosiloxane resin.

21. The method of claim 15, wherein the gel contains an additive.

22. The method of claim 21, wherein the additive is a topical medication or an emollient.

23. The method of claim 19, wherein the closure strip is approximately the width of the bandage.

* * * * *

UNITED STATES PATENT AND TRADEMARK OFFICE
CERTIFICATE OF CORRECTION

PATENT NO. : 7,101,349 B1 Page 1 of 1
APPLICATION NO. : 10/825766
DATED : September 5, 2006
INVENTOR(S) : David M. Binder et al.

It is certified that error appears in the above-identified patent and that said Letters Patent is hereby corrected as shown below:

<u>In the first paragraph of the patent, col. 1, line 3</u>

The word "continuation" should read --division--

<u>In the first paragraph of the patent, col. 1, line 6</u>

The date "Aug. 18" should read --Aug. 21--

<u>In claim 15, col. 6, line 27</u>

The word "loon" should read --loop--.

Signed and Sealed this

Seventh Day of August, 2007

JON W. DUDAS
*Director of the United States Patent and Trademark Office*